US00PP07992P

United States Patent [19]

Hesse

[11] Patent Number: Plant 7,992

[45] Date of Patent: Sep. 29, 1992

[54] CHRYSANTHEMUM PLANT NAMED HOLLY

[75] Inventor: Peter S. Hesse, Nipoma, Calif.

[73] Assignee: Yoder Brothers, Inc., Barberton, Ohio

[21] Appl. No.: 659,556

[22] Filed: Jan. 8, 1991

[51] Int. Cl.[5] ..... A01H 5/00

[52] U.S. Cl. ..... Plt./78

[58] Field of Search ..... Plt./74, 78

[56] References Cited

U.S. PATENT DOCUMENTS

P.P. 5,661 2/1986 Meek et al. ..... Plt. 78

*Primary Examiner*—James R. Feyrer

*Attorney, Agent, or Firm*—Foley & Lardner

[57] ABSTRACT

A Chrysanthemum plant named Holly particularly characterized by its round pompon capitulum form; formal decorative capitulum type; yellow ray floret color; diameter across face of capitulum of 35 to 38 mm. when fully opened; spreading branching pattern, with 6 to 8 breaks after pinch when grown outside under natural daylength in fall flowerings, and 4 to 7 breaks after pinch when grown in 10 cm. pots for spring flowerings; natural season flowering date of August 23 when planting rooted cuttings June 20 in Salinas, Calif., and September 24 to 27 when planting rooted cuttings June 15 to June 18 in Highstown, N.J.; flowering response of 44 to 49 days after rooting in no light/no shade programs in spring; plant height of 35 to 38 cm. when grown in fall under natural daylength with no growth regulators, and 20 to 23 cm. when grown in 10 cm. pots in spring with 1 to 2 applications of 2500 ppm B-9 SP; and durable, uniform performance.

3 Drawing Sheets

The present invention comprises a new and distinct cultivar of Chrysanthemum, botanically known as *Dendranthema grandiflora*, and referred to by the cultivar name Holly.

Holly, identified as 88-#02270, was originated from a cross made by Peter S. Hesse in a controlled breeding program in Parrish, Fla., in 1984.

The female parent of Holly was an unnamed seedling, identified as FG1-6054-WS.

The male parent of Holly was the cultivar Hawkeye, disclosed in U.S. Plant Pat. No. 4,807.

Holly was discovered and selected as one flowering plant within the progeny of the stated cross by Peter S. Hesse in October of 1984, in a controlled environment in Parish, Fla.

The first act of asexual reproduction of Holly was accomplished when vegetative cuttings were taken from the initial selection in December 1984 in a controlled environment in Parrish, Fla., by technicians working under the supervision of Peter S. Hesse.

Horticultural examination of controlled flowerings of successive plantings has shown that the unique combination of characteristics as herein disclosed for Holly are firmly fixed and are retained through successive generations of asexual reproduction.

Holly has not been observed under all possible environmental conditions. The phenotype may vary significantly with variations in environment such as temperature, light intensity and daylength.

The following observations, measurements and comparisons describe plants grown in controlled open areas in Salinas, Calif., and in Highstown, N.J. Rooted cuttings were established in soil and maintained outdoors under the natural temperature and daylength prevailing during June through October. Spring flowerings were conducted in Salinas, Calif., under greenhouse conditions which approximate those generally used in commercial greenhouse practice for small pot spring garden mum production.

The following traits have been repeatedly observed and are determined to be basic characteristics of Holly, which, in combination, distinguish this Chrysanthemum as a new and distinct cutivar:

1. Round pompon capitulum form.
2. Formal decorative capitulum type.
3. Yellow ray floret color.
4. Diameter across face of capitulum of 35 to 38 mm. when fully opened.
5. Branching pattern is spreading and prolific, with 6 to 8 breaks after pinch when grown outside under natural daylength in fall flowerings, and 4 to 7 breaks after pinch when grown in 10 cm. pots for spring flowerings.
p 6. Natural season flower date of August 23 when planting rooted cuttings on June 20 in Salinas, Calif., and of September 24 to 27 when planting rooted cuttings June 15 to June 18 in Highstown, N.J.
7. Flowering response of 44 to 49 days after rooting in no light/no shade programs in spring.
8. Plant height of 35 to 38 cm. when grown in fall under natural daylength with no growth regulators, and of 20 to 23 cm. when grown in 10 cm. pots in spring with 1 to 2 applications of 2500 ppm B-9 SP.
9. Durable, uniform performance.

The accompanying photographic drawings show typical inflorescence and leaf characteristics of Holly, with the colors being as nearly true as possible with illustrations of this type.

Sheet 1 is a color photograph of Holly grown as a pinched spray pot mum with 4 cuttings in a 15 cm. pot.

Sheet 2 is a black and white photograph of three views of the inflorescence of Holly.

Sheet 3 is a black and white photograph showing the upper and under sides of the leaves of Holly at three stages of development (mature, intermediate and immature).

In sheets 2 and 3 a measuring tape in centimeters has been added.

Of the commercial cultivars known to the inventor, the most similar in comparison to Holly is the cultivar identified as Goldmine, disclosed in U.S. Plant Pat. No. 5,661. Reference is made to attached Chart A which compares certain characteristics of Holly to the same characteristics of Goldmine.

Similar traits are ray floret color, capitulum form and type, and branching pattern. Holly has an average of one break per plant less than Goldmine in natural fall flowerings, only one of which was conducted in Salinas. Holly has a faster flowering response than Goldmine in all flowerings. Also, Holly has a taller plant height than Goldmine. In additions, Goldmine has very few disc florets, while Holly has many disc florets, as can be seen in the photographic drawings. Since filing for the patent of Goldmine on Jul. 15, 1983, more detailed information from different locations has been collected for Goldmine, which information is presented in Chart A.

In the following description color references are made to The Royal Horticultural Society Colour Chart. The color values were determined on plant material grown as a pinched spray pot mum in Salinas, Calif., on May 3, 1990.

Classification:

*Botanical.*—*Dendranthema grandiflora* cv. Holly.

*Commercial.*—Round pompon formal decorative spray pot mum and garden mum.

INFLORESCENCE

A. Capitulum:

*Form.*—Round pompon.

*Type.*—Formal decorative.

*Diameter across face.*—35 to 38 mm. when fully opened.

B. Corolla of ray florets:

*Color (general tonality from a distance of three meters).*—Yellow.

*Color.*—Upper surface: 13A to 13B. Under surface: 12A to 12B.

*Shape.*—Spooned, straight.

C. Corolla of disc florets:

*Color (mature).*—13A.

*Color (immature).*—13A, very slightly overlaid with 144B.

Reproductive Organs:

*Androecium.*—Present on disc florets only; moderate pollen.

*Gynoecium.*—Present on both ray and disc florets.

PLANT

A. General Appearance:

*Height.*—35 to 38 cm. when grown in fall under natural daylength with no growth regulators, and 20 to 23 cm. when grown in 10 cm. pots in spring with 1 to 2 applications of 2500 ppm B-9 SP.

*Branching pattern.*—Spreading with 6 to 8 breaks after pinch when grown outside under natural daylength in fall flowerings, and 4 to 7 breaks after pinch when grown in 10 cm. pots for spring flowerings.

B. Foliage:

*Color (upper surface).*—147A.

*Color (under surface).*—147B.

*Shape.*—See photograph.

CHART A

COMPARISON OF HOLLY AND GOLDMINE

| CHARACTERISTIC | HOLLY | GOLDMINE |
|---|---|---|
| Ray floret color | Yellow | Yellow |
| Capitulum form and type | Round pompon formal decorative | Round pompon formal decorative |
| Diameter across face of capitulum | 35 to 38 mm. | 35 to 45 mm. |
| Branching pattern | Spreading | Spreading |
| Breaks, fall, outdoors | 6 to 8 | 7 to 9 |
| Breaks in 10 cm. pots | 4 to 7 | 7 to 9 |
| Natural season flower date: | | |
| Salinas, California | August 23 | August 26 to 29 |
| Hightstown, New Jersey | September 24 to 27 | Sep. 25 to Oct. 3 |
| Flowering response in spring | 44 to 49 days | 53 to 55 days |
| Plant height: | | |
| Natural season fall | 35 to 38 cm. | 20 to 25 cm. |
| 10 cm. pots spring | 20 to 23 cm. | 15 to 18 cm. |

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Holly, as described and illustrated.

* * * * *

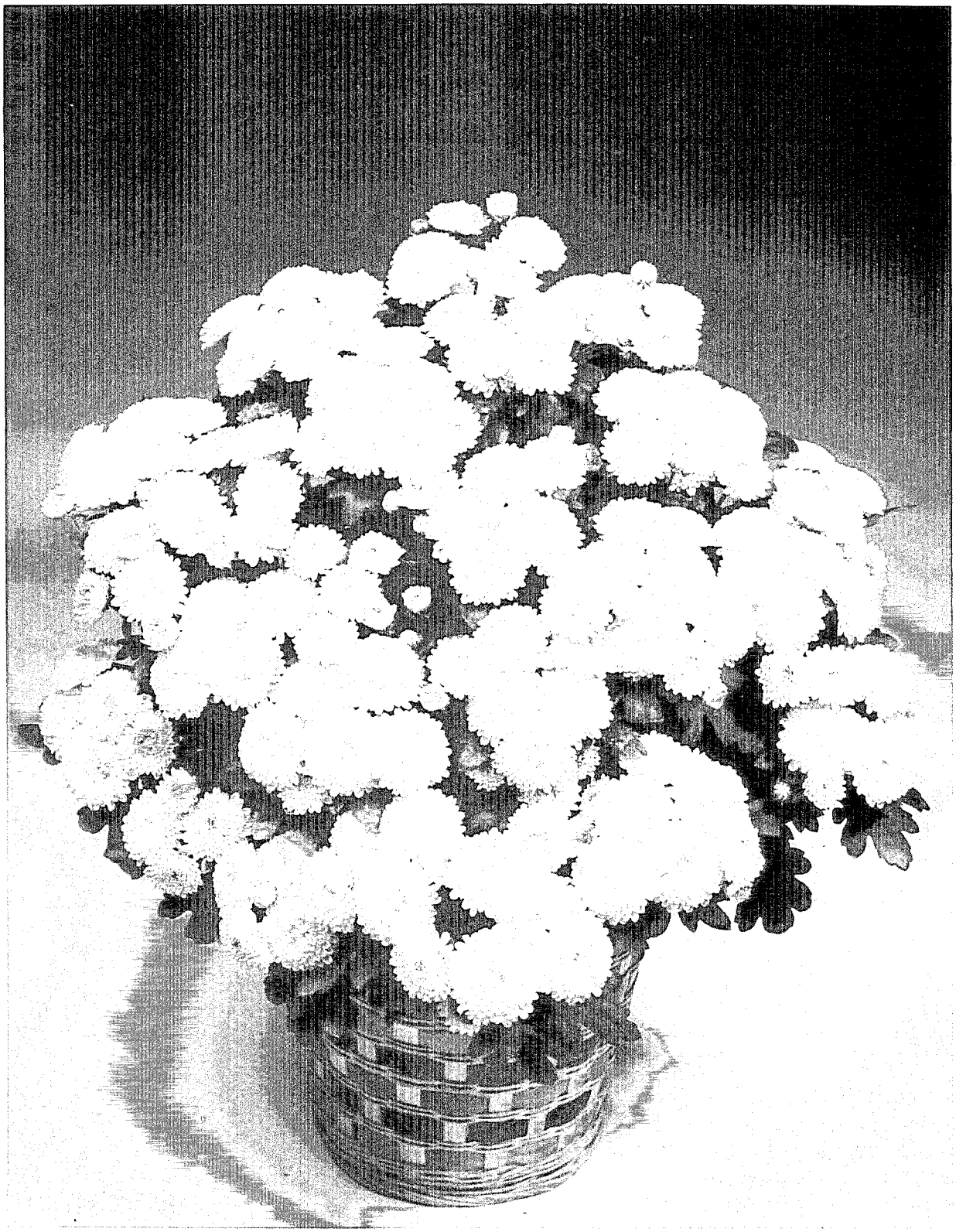

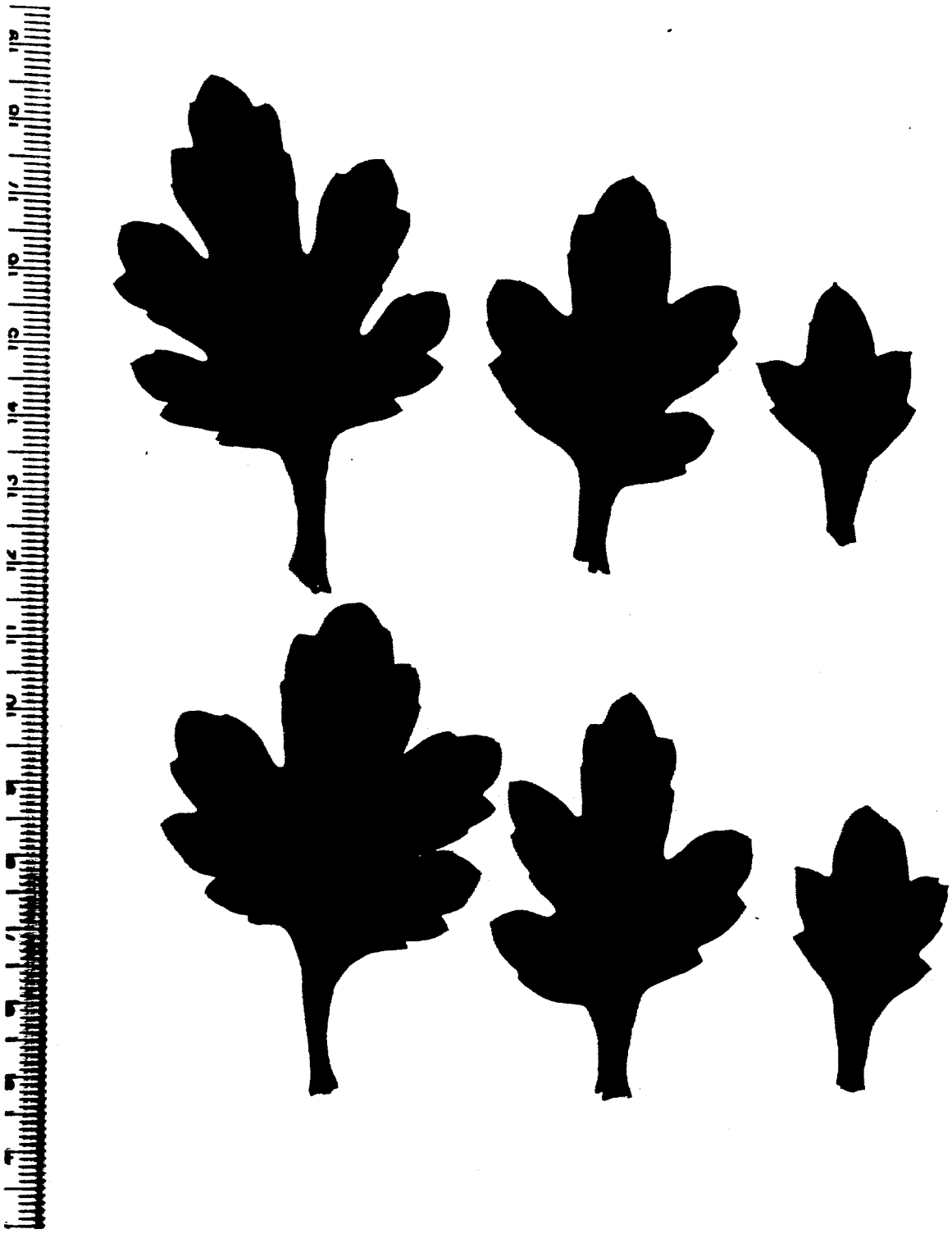

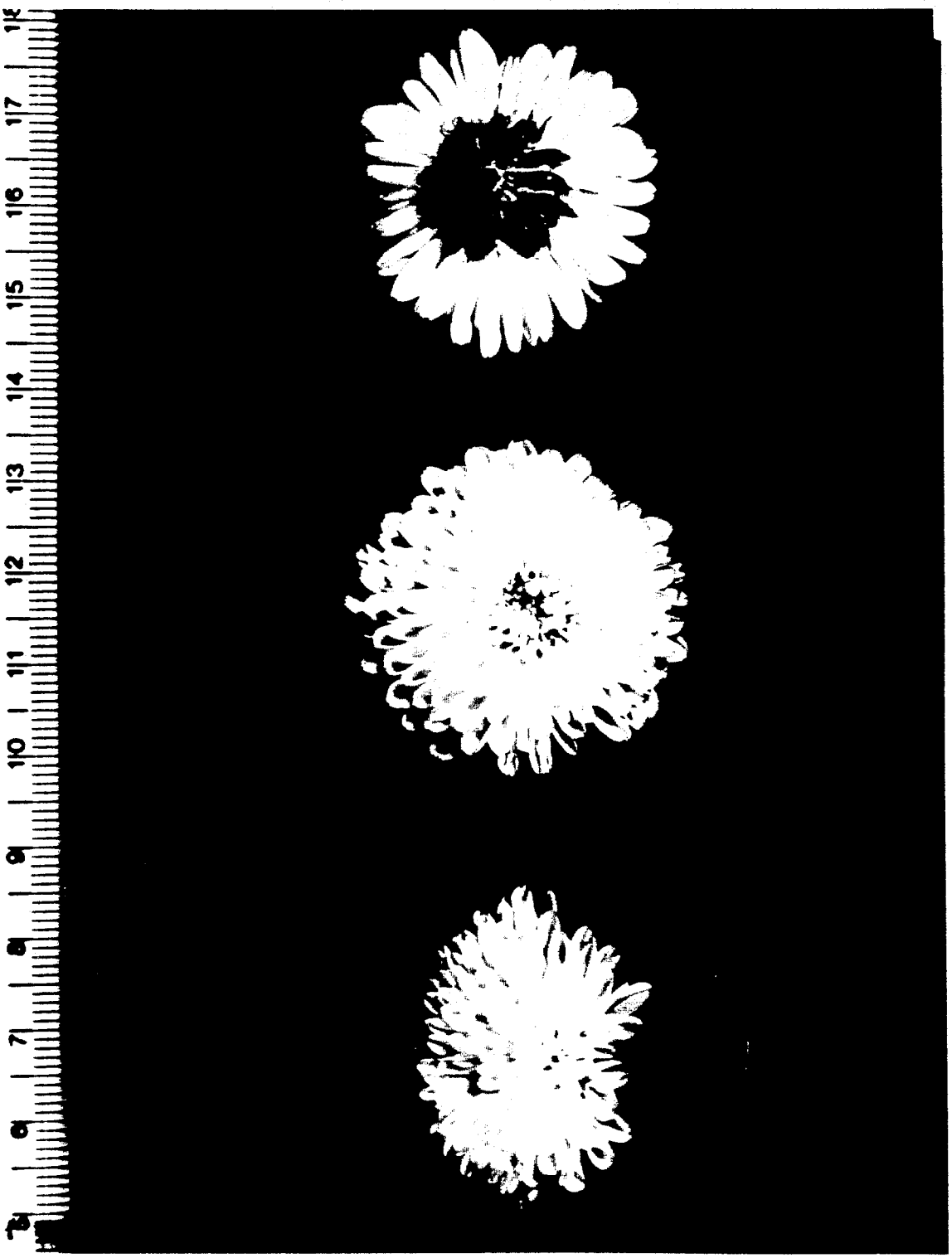
6
7
8
9
10
11
12
13
14
15
16
17
18